(12) United States Patent
Zhang et al.

(10) Patent No.: US 9,398,968 B2
(45) Date of Patent: Jul. 26, 2016

(54) METHOD AND DEVICE FOR LOADING MEDICAL APPLIANCE WITH DRUGS AND/OR POLYMERS

(75) Inventors: Jie Zhang, Shanghai (CN); Bo Yi, Shanghai (CN); Changsheng Wu, Shanghai (CN); Zhirong Tang, Shanghai (CN); Qiyi Luo, Shanghai (CN)

(73) Assignee: SHANGHAI MICROPORT MEDICAL (GROUP) CO., LTD., Pudong New Area, Shanghai (CN)

( * ) Notice: Subject to any disclaimer, the term of this patent is extended or adjusted under 35 U.S.C. 154(b) by 429 days.

(21) Appl. No.: 13/387,927

(22) PCT Filed: Jul. 9, 2010

(86) PCT No.: PCT/CN2010/075077
§ 371 (c)(1),
(2), (4) Date: Jan. 30, 2012

(87) PCT Pub. No.: WO2011/012045
PCT Pub. Date: Feb. 3, 2011

(65) Prior Publication Data
US 2012/0135132 A1 May 31, 2012

(30) Foreign Application Priority Data
Jul. 30, 2009 (CN) .......................... 2009 1 0055719

(51) Int. Cl.
*A61F 2/915* (2013.01)
*G06T 7/00* (2006.01)

(52) U.S. Cl.
CPC .............. *A61F 2/915* (2013.01); *G06T 7/0042* (2013.01); *A61F 2230/0054* (2013.01);
(Continued)

(58) Field of Classification Search
USPC ............... 427/2.24, 2.25, 2.28, 2.3, 261, 286, 427/287; 623/1.46
See application file for complete search history.

(56) References Cited

U.S. PATENT DOCUMENTS 6,395,326 B1 * 5/2002 Castro et al. ................. 427/2.24
2005/0222676 A1 10/2005 Shanley et al.
(Continued)

FOREIGN PATENT DOCUMENTS

CN 1287872 12/2006
CN 1299836 2/2007
(Continued)

OTHER PUBLICATIONS

Unknown, XCaliper, 1995, Meyer Instruments, http://www.meyerinst.com/html/optimas/xcal.htm.*
(Continued)

*Primary Examiner* — Andrew Bowman
(74) *Attorney, Agent, or Firm* — Michael Best & Friedrich LLP (57) ABSTRACT

A method for loading a medical appliance with a medicament and/or a polymer is disclosed, the medical appliance comprising one or more grooves or holes loaded with the medicament and/or polymer. The method comprising the steps of: 1) capturing an image of the grooves or holes of the medical appliance, wherein the image contains at least one complete pattern of the grooves or holes; 2) performing digital image processing on the captured image to obtain the pattern of the grooves or holes; 3) calculating a central position of the pattern of the grooves or holes, and determining an actual central position of the grooves or holes based on the central position; 4) adjusting a relative position of a loading device to the medical appliance to align an outlet of the loading device with the actual central position of the grooves or holes; and 5) opening the outlet of the loading device to load the grooves or holes. A device for loading a medical appliance with a medicament and/or a polymer is further disclosed.

18 Claims, 4 Drawing Sheets

(52) U.S. Cl.
CPC .. *A61F 2240/001* (2013.01); *A61F 2250/0068* (2013.01); *G06T 2207/10004* (2013.01); *G06T 2207/30164* (2013.01)

(56) References Cited

U.S. PATENT DOCUMENTS

| | | |
|---|---|---|
| 2006/0222679 A1 | 10/2006 | Shanley et al. |
| 2006/0222755 A1 | 10/2006 | Diaz et al. |
| 2008/0077218 A1 | 3/2008 | McMorrow et al. |
| 2010/0262230 A1* | 10/2010 | Vecerina et al. ............ 623/1.46 |

FOREIGN PATENT DOCUMENTS

| | | |
|---|---|---|
| WO | 2004012784 | 2/2004 |
| WO | 2004026182 | 4/2004 |
| WO | 2011012045 | 2/2011 |
| WO | 2011088755 | 7/2011 |

OTHER PUBLICATIONS

PCT/CN2010/075077 International Search Report dated Oct. 21, 2010 (4 pages).

* cited by examiner

METHOD AND DEVICE FOR LOADING MEDICAL APPLIANCE WITH DRUGS AND/OR POLYMERS

CROSS-REFERENCE TO RELATED APPLICATIONS

This application is a national stage filing under 35 U.S.C. 371 of International Application No. PCT/CN2010/075077, filed Jul. 9, 2010, which claims priority benefits to Chinese Patent Application No. 200910055719.4, filed Jul. 30, 2009. These applications are incorporated herein by reference in their entirety.

TECHNICAL FIELD

The present invention relates to a method and a device for loading a medical appliance with a medicament and/or polymer, and particularly to a method and a device for loading a drug eluting stent with a medicament.

BACKGROUND

There are thousands of patients in China suffering severe coronary atherosclerotic heart diseases who need a percutaneous transluminal coronary angioplasty (PTCA) and a stent placement annually. However, 30% of the patients subject to such operations will be faced with the problem of narrowing of blood vessels within half a year. After blood vessel dilation operations, these patients will generate many cells that block blood vessels due to failure in normal rehabilitation. As a result, they need one more bypass grafting operation or angioplasty.

In recent years, a new method capable of inhibiting cell division is invented in the medical circle, i.e., a drug eluting stent, which coats the stent for dilating blood vessels of a patient with a medicament that releases an antibiotic capable of inhibiting growth of abnormal cells. Thus, the blood vessels will not be blocked by cells and thereby will not become narrow.

Usually, the drug eluting stent carries a medicament via a polymer coated on the surface of a bare metal stent. When the stent is implanted into a lesion site within a blood vessel, the medicament releases controllably in a manner of eluting from the polymer coating into cardiovascular wall tissue to exert biological effect. At present, for most existing drug eluting stents, usually an active medicament and a polymer are mixed and coated on the partial or entire surface of the bare stent. In clinic application, such medicament stent having a polymer coating can reduce the incidence of narrowing again to below 10%. However, such drug eluting stent possibly leads to formation of a thrombus after being implanted into a human body due to a continuous decrease in the medicament and a correspondingly continuous increase in the polymer concentration.

Accordingly, the existing technology puts forward a nanoscale aperture releasing architecture for a drug eluting stent, which opens the drug eluting stent with a plurality of nanoscale apertures thereon to effectively control the medicament release rate and reduce the risk of incurring a thrombus after implantation of the drug eluting stent into human body tissues. But such architecture needs to coat the nanoscale apertures with a traditional method, such as a coating method etc. The defect of the method lies in failure in precisely loading a desirable part with a medicament. Especially for a stent with rather small grooves or holes for being loaded with a medicament, it is more difficult for the traditional method to precisely identify and locate positions of the grooves, and thus unable to provide bases for medicament loading processes.

Besides, in the known technology, a large amount of non-deformable small apertures capable of storing a medicament, which are called medicament storage grooves are processed on the surface of a bare metal stent. These storage grooves can provide medicament eluting, whereby it is not necessary any more for a medicament to be coated on the stent surface but to be buried in the storage grooves together with a biodegradable polymer. Such technology can realize a positional release of medicament, and has higher precision. Such manner can control not only the medicament eluting time but also the medicament eluting rate.

However, the bare metal stent with medicament storage grooves is formed from etching a tube with a laser technique. The processed bare metal stent will undergo a displacement of actual positions of the medicament storage grooves in relative to theoretical designed positions caused by the elastic deformation of itself and the process of manual pickup and placement. Since the medicament grooves have very small dimensions, usually about 20 to 80 microns, if a dispensing device still performs the dispensing operation at the designed position, the medicament will be dispensed outside the grooves. After the stent is implanted into a human body, the medicament formed outside the grooves will peel off the stent, thereby causing formation of a thrombus.

SUMMARY OF INVENTION

The object of the present invention is to provide a method and a device for placing a medicament and/or polymer on a medical appliance, wherein a medicament groove can be precisely dispensed to based on the actual position of a stent groove/or hole thereby avoiding the circumstance in which the medicament and/or polymer is dispensed outside the groove and reducing the risk of forming a thrombus.

In order to realize the aforesaid object, the present invention provides a method for loading a medical appliance with a medicament and/or polymer, the medical appliance having one or more grooves or holes for being loaded with the medicament and/or polymer, characterized in comprising steps of:
1) capturing an image of the grooves or holes of the medical appliance, the image comprising at least one complete pattern of the grooves or holes;
2) performing digital image processing on the captured image to obtain the pattern of the grooves or holes;
3) calculating a central position of the pattern of the grooves or holes, and determining an actual central position of the grooves or holes based on the central position;
4) adjusting a relative position of a loading device to the medical appliance to align an outlet of the loading device with the actual central position of the grooves or holes; and
5) opening the outlet of the loading device to load the grooves or holes.

It should be noted that the so-called "digital image processing" in the present invention means a process of converting an image signal into a digital signal and processing it by using a computer. Besides, the so-called "grooves or holes" in the present invention include through grooves or holes or non-through grooves or holes. Non-through grooves or holes are preferred in the present invention.

Preferably, in step 2), converting the captured image into a set of pixel points and performing the digital image processing on the set of pixel points to obtain the pattern of the grooves or holes. More preferably, in step 2), after the image is converted into the set of pixel points, values are assigned to the pixel points based on a gray value of each of the pixel points and a pixel point conforming with a preset value or value range is designated as a target pixel point or a background pixel point, and all the pixel points designated as the target pixel points or the background pixel points are connected to form a target pixel body. Particularly, a value can be assigned to each of the pixel values via processing the pixel point with a binary method.

In one mode of the present invention, in step 3), a spatial coordinate of a central pixel point of the pattern of the grooves or holes is calculated based on a spatial coordinate of each of the pixel points in the pattern of the grooves or holes. More preferably, step 4) further comprises the step of determining a spatial coordinate of a geometrical center of the captured image.

It should be pointed out herein that the so-called "geometrical center" in the present invention means a crossing point of two vertically intersected lines in a picture. In the method according to the present invention, the position for capturing an image does not vary with the movement of the medical appliance, so when the medical appliance having grooves or holes is moved, only the spatial coordinate of the central position of the pattern changes whereas the spatial coordinate of the geometrical center of the image doesn't change. In the present invention, the spatial coordinate of the geometrical center of the image corresponds to the spatial coordinate of the center of the image capturing device. That is, only when the image capturing device is moved, the position of the geometrical center of the image changes.

Preferably, the spatial coordinate of the geometrical center of the image can be determined by the following approach:
  a) obtaining spatial coordinates of four apexes of the captured image;
  b) calculating the spatial coordinate of the geometrical center of the captured image based on the spatial coordinates of the four apexes.

In another mode of the present invention, in step 3), a pixel coordinate of the central pixel point of the pattern of the grooves or holes is calculated based on a pixel coordinate of each of the pixel points in the pattern of the grooves or holes.

Preferably, step 4) further comprises determining a pixel coordinate of the pixel point at the geometrical center of the captured image.

Preferably, in step 4), the pixel coordinate of the geometrical center of the captured image is determined by the following approach:
  a) obtaining pixel coordinates of four apexes of the captured image;
  b) calculating the pixel coordinate of the geometrical center of the captured image based on the pixel coordinates of the four apexes Alternatively, in step 4), medium values of the pixel points can be obtained respectively in the x direction and in the y direction based on a resolution of the captured image to determine the pixel coordinate of the geometrical center of the captured image.

After the pixel coordinate of the geometrical center of the image is determined, in step 4), a coordinate difference value between the pixel coordinate of the central pixel point of the pattern and the pixel coordinate of the pixel point at the geometrical center of the image is calculated, and the calculated pixel coordinate difference value is converted into a spatial coordinate difference value.

Preferably, after the coordinate difference value between the spatial coordinate of the central position of the pattern of the grooves or holes and the spatial coordinate of the geometrical center is determined, in step 4), the medical appliance having the grooves or holes is moved in the x direction and/or in the y direction based on the coordinate difference value to cause the actual central position of the grooves or holes and the geometrical center to be in the same longitudinal axis. Or preferably, in step 4), the image capturing device is moved in the x direction and/or in the y direction based on the coordinate difference value to cause the actual central position of the grooves or holes and the geometrical center to be in the same longitudinal axis.

Preferably, the method according to the present invention further comprises predetermining a positional relationship between the outlet of the loading device and the center of the image capturing device to obtain a spatial coordinate difference value between the outlet of the loading device and the center of the image capturing device in the x direction and/or in the y direction.

Preferably, after the actual central position of the grooves or holes and the geometrical center are caused to be in the same longitudinal axis, the medical appliance is moved in the x direction and/or in the y direction based on the obtained spatial coordinate difference value between the outlet of the loading device and the center of the image capturing device to cause the outlet of the loading device and the actual central position of the grooves or holes to be in the same longitudinal axis. Or preferably, after the actual central position of the grooves or holes and the geometrical center are caused to be in the same longitudinal axis, the outlet of the loading device is moved in the x direction and/or in the y direction based on the obtained spatial coordinate difference value between the outlet of the loading device and the center of the image capturing device to cause the outlet of the loading device and the geometrical center to be in the same longitudinal axis.

Preferably, the method according to the present invention further comprises step 6), in which the medical appliance is moved back to a position where the medical appliance is captured in step 2) and then rotated by a certain angle and/or translated by a step pitch. Then step 2) to step 6) are performed repeatedly till the medicament and/or polymer is dispensed to all the grooves or holes of the medical appliance.

Preferably, the width of the grooves or holes is within a range from 0.5 to 200 microns. More preferably, the width of the grooves or holes is within a range from 20 to 80 microns.

Preferably, the medical appliance is a human body endoluminal stent. More preferably, the human body endoluminal stent is a blood vessel stent.

Preferably, the medicament includes a chemical medicament and/or a bioactive substance. More preferably, the chemical medicament includes an immunosuppressant and/or anticancer medicament, the bioactive substance includes protein, polypeptide, DNA, RNA and/or microRNA. Particularly, the immunosuppressant is selected from rapamycin and derivatives thereof, and the anticancer medicament is selected from paclitaxel and derivatives thereof.

Preferably, the polymer is a biodegradable polymer.

Preferably, the biodegradable polymer is one or more selected from homopolymers or copolymers of $C_2$-$C_6$ acyclic hydroxycarboxylic acid composed of C, H, and O.

Preferably, the biodegradable polymer is:
  (1) one or more of homopolymers of D-lactic acid, L-lactic acid, glycolic acid or g-caprolactone;
  (2) one or more of copolymers formed by more than any two from D-lactic acid, L-lactic acid, glycolic acid and g-caprolactone as monomers Preferably, the biodegradable polymer is one or more selected from poly D,L-lactide, poly D-lactide, poly L-lactide, polyglycolide, poly(glycolide-lactide) and poly g-caprolactone.

Preferably, the loading device comprises a container pre-loaded with the medicament and/or polymer solution.

Preferably, in step 1), the image of the grooves or holes is obtained via a camera or a video camera.

The present invention further provides a device for loading a medical appliance with a medicament and/or a polymer, the medical appliance including one or more grooves or holes for being loaded with the medicament and/or polymer, characterized in that the device comprises:

- a medical appliance placement platform for placing the medical appliance;
- an image capturing device located above the placement platform for capturing an image of the grooves or holes of the medical appliance, the image containing at least one complete pattern of the grooves or holes;
- an image processing unit connected with the image capturing device for performing digital image processing on the captured image to obtain the pattern of the grooves or holes, calculating a central position of the pattern of the grooves or holes, and determining an actual central position of the grooves or holes based on the central position;
- a loading device pre-loaded with the medicament and/or polymer for loading the grooves or holes of the medical appliance via an outlet thereof; and
- a position adjustment device for adjusting a relative positional relation of the medical appliance with the image capturing device and/or the loading device.

Preferably, the image processing unit converts the captured image into a set of pixel points. More preferably, after converting the image into the set of pixel points, the image processing unit assigns values to the pixel points based on a gray value of each of the pixel points, designates a pixel point conforming with a preset value or value range as a target pixel point or a background pixel point, and connects all the pixel points designated as the target pixel points or the background pixel points to form a target pixel body. Particularly, the image processing unit assigns a value to each of the pixel values via processing the pixel point with a binary method.

Preferably, the image processing unit calculates a spatial coordinate of a central pixel point of the pattern of the grooves or holes based on a spatial coordinate of each of the pixel points in the pattern of the grooves or holes.

In one mode of the present invention, the image processing unit can be used for determining a spatial coordinate of a geometrical center of the captured image. Preferably, the image processing unit determines the spatial coordinate of the geometrical center of the captured image by the following approach:

a) obtaining spatial coordinates of four apexes of the captured image;
b) calculating the spatial coordinate of the geometrical center of the captured image based on the spatial coordinates of the four apexes.

In another mode of the present invention, the image processing unit calculates a pixel coordinate of the central pixel point of the pattern of the grooves or holes based on a pixel coordinate of each of the pixel points in the pattern of the grooves or holes.

Preferably, the image processing unit is further used for determining a pixel coordinate of the pixel point at the geometrical center of the captured image. More preferably, the image processing unit determines the pixel coordinate of the pixel point at the geometrical center of the captured image by the following approach:

a) obtaining pixel coordinates of four apexes of the captured image;
b) calculating the pixel coordinate of the geometrical center of the captured image based on the pixel coordinates of the four apexes.

Or more preferably, the image processing unit obtains medium values of the pixel points respectively in the x direction and in the y direction based on a resolution of the image capturing device to determine the pixel coordinate of the geometrical center of the captured image.

Preferably, the image processing unit is capable of calculating a coordinate difference value between the pixel coordinate of the central pixel point of the pattern and the pixel coordinate of the pixel point at the geometrical center of the image, and converting the calculated pixel coordinate difference value into a spatial coordinate difference value.

Preferably, the device according to the present invention further comprises a position calibration device for calibrating a position difference between the outlet of the loading device and the center of the image capturing device and obtaining a spatial coordinate difference value between the outlet of the loading device and the center of image capturing device in the x direction and/or in the y direction.

Preferably, the position adjustment device is connected with the medical appliance placement platform to drive the medical appliance placement platform to move on an x-y horizontal coordinate plane.

Preferably, the position adjustment device is connected with the image capturing device to drive the image capturing device to move on an x-y horizontal coordinate plane.

Preferably, the position adjustment device is connected with the loading device to drive the loading device to move on an x-y horizontal coordinate plane.

Preferably, the image capturing device and the loading device are disposed on the same vertical surface.

Preferably, the medical appliance placement platform comprises a rotation platform, on the rotation platform being provided a stent shaft, and on the stent shaft being placed the medical appliance.

Preferably, the image capturing device is a camera or video camera. More preferably, the image capturing device is an industrial camera or video camera.

In the present invention, each of the grooves or holes of the medical appliance is precisely located with a digital image processing technology and a positioning technology to ensure that an outlet of a loading device is positioned vertically above the center of the medicament grooves or holes. So the circumstance in which the medicament and/or polymer is dispensed outside the grooves can be avoided so that the risk of causing damage to a human body is reduced.

DETAILED DESCRIPTION OF PREFERRED EMBODIMENTS

The present invention is described in detail with reference to the drawings and the embodiments.

Figure 1:
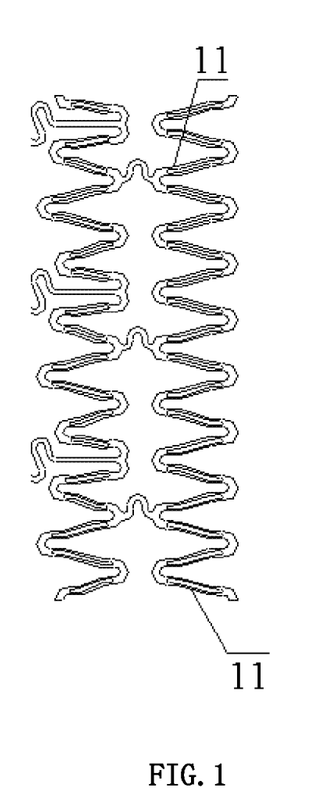
FIG. 1 is an exploded schematic diagram of a drug eluting stent.

As shown in FIG. 1, groove 11 is provided on drug eluting stent 1, and the diameter of groove 11 is about 20 to 80 um. Usually, groove 11 is loaded therein with a medicament and/or polymer.

The medicament includes a chemical medicament and/or bioactive substance.

The chemical medicament includes an immunosuppressant and/or anticancer medicament, and the bioactive substance includes protein, polypeptide, DNA, RNA and/or microRNA.

The immunosuppressant is selected from rapamycin or derivatives thereof, and the anticancer medicament is selected from paclitaxel or derivatives thereof.

The polymer is a biodegradable polymer. The biodegradable polymer is one or more selected from homopolymers or copolymers of $C_2$-$C_6$ acyclic hydroxycarboxylic acid composed of C, H, and O.

Alternatively, the biodegradable polymer is:
(1) one or more of homopolymers of D-lactic acid, L-lactic acid, glycolic acid or ε-caprolactone; and/or
(2) one or more of copolymers formed by more than any two from D-lactic acid, L-lactic acid, glycolic acid and ε-caprolactone as monomers.

Alternatively, the biodegradable polymer is one or more selected from poly D,L-lactide, poly D-lactide, poly L-lactide, polyglycolide, poly(glycolide-lactide) and poly ε-caprolactone.

Embodiment 1

Figure 2:
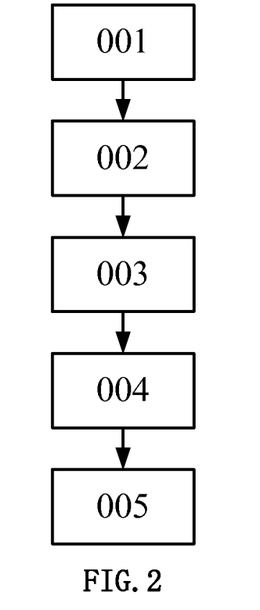
FIG. 2 is a flow chart of one embodiment of the method according to the present invention.

As shown in FIG. 2, in the loading method according to the present invention, firstly in step 001, the positional relationship between the outlet of the loading device and the center of the image capturing device is determined to obtain spatial coordinate difference value M in the x direction and/or spatial coordinate difference value N in the y direction between the outlet of the loading device and the center of the image capturing device.

In step 002, the image of groove 11 on drug eluting stent 1 is captured, and the image includes at least one complete groove 11.

Subsequently in step 002, the captured image is converted into a set of pixel points first. After the image is converted into the set of pixel points, values are assigned to the pixel points based on a gray value of each of the pixel points via processing the pixel point with a binary method, and a pixel point conforming with a preset value or value range is designated as a target pixel point or a background pixel point, and all the pixel points designated as the target pixel points or background pixel points are connected to form a target pixel body, i.e., the pattern of groove 11. Thus, the pattern of groove 11 is obtained.

In step 003, pixel point P (not shown) of the central position of the target pixel body is calculated first, and pixel point P is the pixel point of the groove center of groove 11. After pixel point P is obtained, it is converted into the spatial coordinate (A, B).

Subsequently, in step 003, the spatial coordinate (A', B') of the geometrical center of the captured image is determined. The spatial coordinate (A', B') of the geometrical center can be determined by the following means of:
a) obtaining spatial coordinates of four apexes of the captured image;
b) calculating the spatial coordinate of the geometrical center of the captured image based on the spatial coordinates of the four apexes.

Then in step 004, stent 1 is moved in the x direction and/or in the y direction with reference to the spatial coordinate (A', B') of the central position of the image till the spatial coordinate (A, B) of the groove center of the medicament groove accords with the coordinate (A', B'). Then, stent 1 moves towards the loading device in the x direction by M and moves towards the loading device in the y direction by N, so as to cause the outlet of the loading device and the actual central position of the grooves or holes to be in the same longitudinal axis.

Subsequently, in step 005, the outlet of the loading device is opened so that the medicament and/or polymer pre-loaded into the loading device is dispensed in groove 11 of drug eluting stent 1 via its outlet whereby the dispensing operation on one groove 11 of drug eluting stent 1 is fulfilled.

If precise dispensing to all grooves 11 of one stent 1 is desired, after the completion of the aforesaid step 005, step 006 is added. That is, when the dispensing operation on one medicament groove 11 of stent 1 is completed, step 006 is performed, in which the stent 1 is firstly moved back to the position where the stent 1 is captured in step 002 and then the stent 1 is rotated by a certain angle and/or translated by a certain step pitch. When step 006 is completed, steps 002-005 are performed again to perform the dispensing operation on one of the remaining grooves which are not yet dispensed to. Similarly, a repeated operation is performed till the medicament and/or polymer is dispensed to all the grooves on stent 1.

For each groove 11 of drug eluting stent 1, searching for and positioning the groove center are performed respectively, therefore precise dispensing can be fulfilled in such manner of the medicament and/or polymer being loaded.

Embodiment 2

In another embodiment of the loading method according to the present invention, in step 003, pixel point P (not shown) of the central position of the target pixel body is still calculated first, and the pixel coordinate (a, b) of pixel point P is obtained. Then, the pixel coordinate (a', b') of the geometrical center pixel point of the captured image is determined.

In one mode of the present invention, the pixel coordinate of the geometrical center of the captured image is determined with the following approach:
a) obtaining pixel coordinates of four apexes of the captured image;
b) calculating the pixel coordinate of the geometrical center of the captured image based on the pixel coordinates of the four apexes.

In another mode of the present invention, medium values of the pixel points in the x direction and in the y direction may be obtained respectively based on a resolution of the captured image thereby to determine the pixel coordinate (a', b') of the geometrical center of the captured image. For example, for a picture with the resolution of 480×640, the pixel coordinate of the geometrical center of the image is (240, 320).

After the pixel coordinate (a', b') of the geometrical center of the image is determined, a coordinate difference value (a-a', b-b') between the pixel coordinate of the central pixel point of the pattern and the pixel coordinate of the pixel point at the geometrical center of the image is calculated, and the calculated pixel coordinate difference value is converted into a spatial coordinate difference value (A-A', B-B').

Then, in step 004, the medical appliance including the grooves or holes is moved in the x direction and in the y direction based on the spatial coordinate difference value (A-A', B-B') to cause the actual central position of the grooves or holes and the geometrical center to be in the same longitudinal axis.

Embodiment 3

Figure 3:
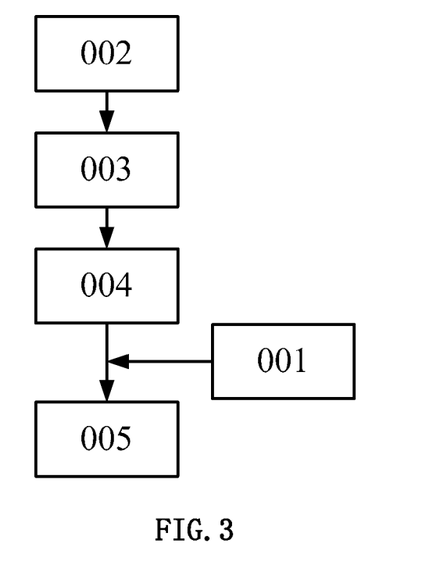
FIG. 3 is a flow chart of another embodiment of the method according to the present invention.

As shown in FIG. 3, in another embodiment of the present invention, step 001 may be performed between step 004 and step 005. In step 004, the image capturing device is moved in the x direction and/or in the y direction based on the spatial coordinate difference value (A-A', B-B') to cause the geometrical center and the actual central position of the grooves or holes to be in the same longitudinal axis. Later, in step 001, a positional relationship between the outlet of the loading device and the center of the image capturing device is further determined to obtain spatial coordinate difference value M' in the x direction and/or spatial coordinate difference value N' in the y direction between the outlet of the loading device and the center of the image capturing device.

Then, stent 1 moves towards the loading device by M' in the x direction, and moves towards the loading device by N' in the y direction, so as to cause the outlet of the loading device and the actual central position of the grooves or holes to be in the same longitudinal axis.

In another embodiment, in step 004, after the actual central position of the grooves or holes of the stent and the geometrical center are in the same longitudinal axis, the loading device may also be moved in addition to the stent to cause the outlet of the loading device and the actual central position of the grooves or holes to be in the same longitudinal axis.

Embodiment 4

Figure 4:
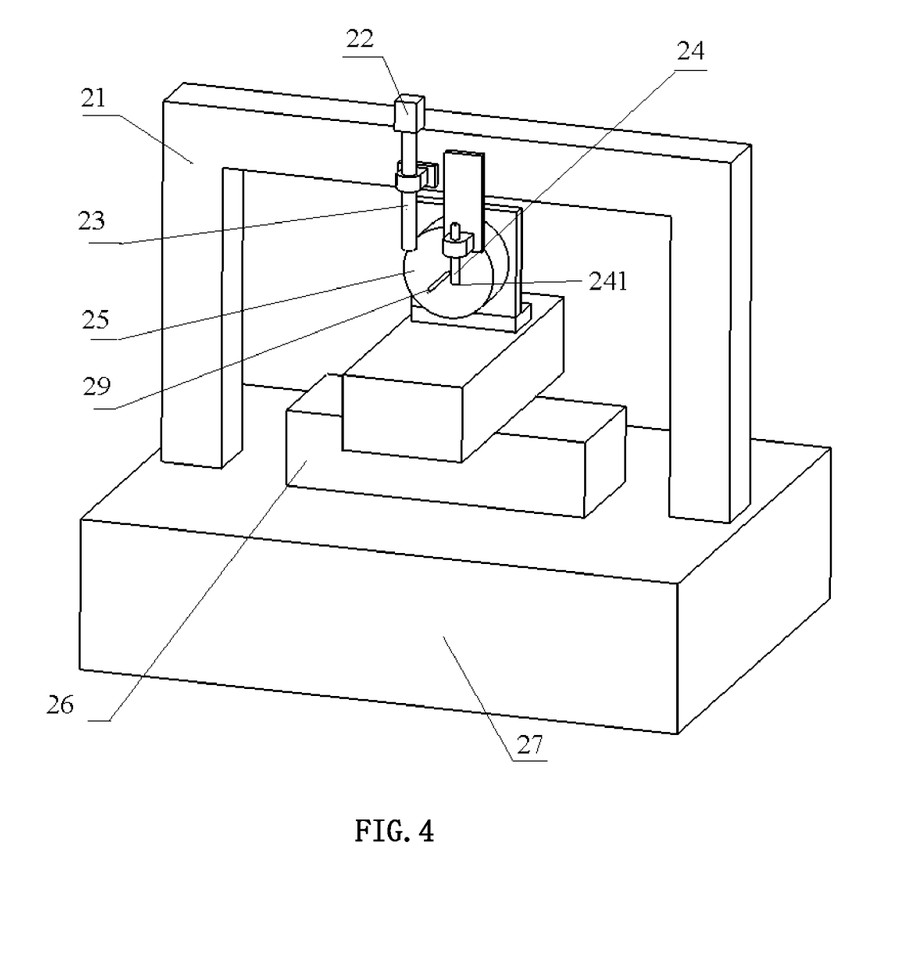
FIG. 4 is a schematic diagram of one embodiment of the loading device according to the present invention.

FIG. 4 shows one embodiment of the loading device according to the present invention. The device for dispensing a medicament to groove 11 of drug eluting stent 1 comprises: gantry 21, image processing device 22, image capturing device 23, loading device 24, rotation platform 25, medical appliance placement platform 26, and base 27.

As shown in FIG. 4, gantry 21 is disposed on base 27 and perpendicular to base 27. Image capturing device 23 is fixed on gantry 21 and perpendicular to a beam of gantry 21.

Image capturing device 23 is connected to image processing device 22. Image processing device 22 receives an image captured by image capturing device 23, and transmits the processed image to a control part of placement platform 26 or to an externally visible part for an operator to proceed with a next operation. Image capturing device 23 can be connected with position adjustment device 28 (not shown) that adjusts loading device 24 according to a received instruction.

Loading device 24 is also fixed on gantry 21, and perpendicular to gantry 21. Loading device 24 is pre-loaded with a medicament and/or polymer.

On base 27 is medical appliance placement platform 26 provided. As shown in FIG. 4, placement platform 26 is composed of a transverse platform, and a longitudinal platform that is disposed above the transverse platform. Placement platform 26 can be connected with position adjustment device 28 (not shown) that drives medical appliance placement platform 26 to move on an x-y horizontal coordinate plane according to a received instruction.

Above medical appliance placement platform 26 is provided with rotation platform 25 that is perpendicular to placement platform 26. As shown in FIG. 4, rotation platform 25 is circular or alternatively can be of another geometrical shape. On rotation platform 25 is stent shaft 29 provided. One end of stent shaft 29 is connected with rotation platform 25, and stent shaft 29 freely rotates on rotation platform 25 by taking the end of its connection to rotation platform 25 as a pivot. Stent 1 is provided on stent shaft 29 as shown.

Moreover, in another embodiment of the present invention, a calibration device is further provided for calibrating a position difference between outlet 241 of loading device 24 and image capturing device 23, i.e., capable of automatically obtaining the numerical values of space M in the x direction and space N in the y direction.

In another embodiment of the present invention, position adjustment device 28 (not shown) has a control chip, image processing device 22 transmits its result to position adjustment device 28 (not shown), and the control chip of position adjustment device 28 (not shown) adjusts placement platform 26 according to the received data.

The technical contents and features of the present invention are disclosed as above. However, it can be understood that under the inventive thoughts of the present invention, the skilled in the art can make various changes and improvement to the aforesaid architecture, but these all belong to the protection scope of the present invention. Depictions of the aforesaid embodiments are exemplary and not restrictive, and the protection scope of the present invention is determined by the claims.

The invention claimed is:

1. A device for loading a medical appliance with a medicament and/or polymer, wherein the medical appliance contains one or more grooves or holes for being loaded with the medicament and/or polymer, characterized in comprising:
    a medical appliance placement platform for placing the medical appliance;
    an image capturing device located above the placement platform for capturing an image of the grooves or holes of the medical appliance, wherein the image contains at least one complete pattern of the grooves or holes;
    an image processing unit connected with the image capturing device, wherein the image processing unit is programmed to perform digital image processing on the image captured by the image capturing device to obtain the pattern of the grooves or holes, to calculate a central position of the pattern of the grooves or holes, and to determine an actual central position of the grooves or holes based on the central position;
    a loading device pre-loaded with the medicament and/or polymer for loading the grooves or holes of the medical appliance via an outlet thereof; and
    a position adjustment device for adjusting a relative positional relation of the medical appliance with the image capturing device and/or the loading device.

2. The device according to claim 1, characterized in that the image processing unit converts the captured image into a set of pixel points, and then assigns values to the pixel points based on a gray value of each of the pixel points, designates a pixel point conforming with a preset value or value range as a target pixel point or a background pixel point, and connects all the pixel points designated as the target pixel points or the background pixel points to form a target pixel body.

3. The device according to claim 1, characterized in that the image processing unit calculates a spatial coordinate of a central pixel point of the pattern of the grooves or holes based on a spatial coordinate of each of the pixel points in the pattern of the grooves or holes;
    the image processing unit is further used for determining a spatial coordinate of a geometrical center of the captured image by the following approach:
    a) obtaining spatial coordinates of four apexes of the captured image;

b) calculating the spatial coordinate of the geometrical center of the captured image based on the spatial coordinates of the four apexes.

4. The device according to claim 1, characterized in that the image processing unit calculates a pixel coordinate of the central pixel point of the pattern of the grooves or holes based on a pixel coordinate of each of the pixel points in the pattern of the grooves or holes;

the image processing unit is further used for obtaining medium values of the pixel points respectively in an x direction and in a y direction based on a resolution of the image capturing device, or determining the pixel coordinate of the geometrical center of the captured image by the following approaches (a) and (b):

(a) obtaining pixel coordinates of four apexes of the captured image;

(b) calculating the pixel coordinate of the pixel point at the geometrical center of the captured image based on the pixel coordinates of the four apexes; and the image processing unit is capable of calculating a pixel coordinate difference value between the pixel coordinate of the central pixel point of the pattern and the pixel coordinate of the pixel point at the geometrical center of the image, and capable of converting the pixel coordinate difference value into a spatial coordinate difference value.

5. The device according to claim 1, characterized in further comprising a position calibration device for calibrating a position difference between an outlet of the loading device and the image capturing device and obtaining a spatial coordinate difference value between the outlet of the loading device and the image capturing device in an x direction and/or in a y direction.

6. The device according to claim 1, characterized in that the position adjustment device is connected with the medical appliance placement platform to drive the medical appliance placement platform to move on an x-y horizontal coordinate plane.

7. The device according to claim 1, characterized in that the position adjustment device is connected with the image capturing device to drive the image capturing device to move on an x-y horizontal coordinate plane.

8. The device according to claim 1, characterized in that the position adjustment device is connected with the loading device to drive the loading device to move on an x-y horizontal coordinate plane.

9. The device according to claim 1, characterized in that the image capturing device and the loading device are disposed on a common vertical surface.

10. The device according to claim 1, characterized in that the medical appliance placement platform comprises a rotation platform, on the rotation platform being provided a stent shaft, and on the stent shaft being placed the medical appliance.

11. A method for loading a medical appliance with a medicament and/or polymer using the device of claim 1, wherein the medical appliance contains one or more groves or holes for being loaded with the medicament and/or polymer, characterized in comprising steps of:

a) positioning the medical appliance on the medical appliance placement platform;

b) capturing an image of the grooves or holes of the medical appliance with the image capturing device located above the placement platform, wherein the image contains at least one complete pattern of the grooves or holes;

c) performing digital image processing on the captured image, with the image processing unit connected with the image capturing device, to obtain the pattern of the grooves or holes;

d) calculating, with the image processing unit, a central position of the pattern of the grooves or holes and determining an actual central position of the grooves or holes, with the image processing unit, based on the central position;

e) adjusting, with the position adjustment device, a relative position of a loading device to the medical appliance to align an outlet of the loading device with the actual central position of the grooves or holes, wherein the loading device is pre-loaded with the medicament and/or polymer; and f) opening the outlet of the loading device to load the grooves or holes.

12. The method according to claim 11, characterized in, in step 2), converting the captured image into a set of pixel points and performing digital image processing on the set of the pixel points to obtain the pattern of the grooves or holes; and after converting the image into the set of the pixel points, assigning values to the pixel points based on a gray value of each of the pixel points, designating a pixel point conforming with a preset value or value range as a target pixel point or a background pixel point, and connecting all the pixel points designated as the target pixel points or the background pixel points to form a target pixel body.

13. The method according to claim 11, characterized in, in step 3), calculating a spatial coordinate of a central pixel point of the pattern of the grooves or holes based on a spatial coordinate of each of the pixel points in the pattern of the grooves or holes; and Step 4) further comprises determining a spatial coordinate of a geometrical center of the captured image by the following approach:

a) obtaining spatial coordinates of four apexes of the captured image;

b) calculating the spatial coordinate of the geometrical center of the captured image based on the spatial coordinates of the four apexes.

14. The method according to claim 13, characterized in, in step 3), calculating a pixel coordinate of the central pixel point of the pattern of the grooves or holes based on a pixel coordinate of each of the pixel points in the pattern of the grooves or holes;

a) obtaining pixel coordinates of four apexes of the captured image;

b) calculating the pixel coordinate of the geometrical center of the captured image based on the pixel coordinates of the four apexes; and in step 4), calculating a coordinate difference value between the pixel coordinate of the central pixel point of the pattern and the pixel coordinate of the pixel point at the geometrical center of the image, and converting the calculated pixel coordinate difference value into a spatial coordinate difference value.

15. The method according to claim 14, characterized in, in step 4), moving the medical appliance having the grooves or holes in the x direction and/or in the y direction based on the coordinate difference value between the spatial coordinate of the central position of the pattern of the grooves or holes and the spatial coordinate of the geometrical center to cause the actual central position of the grooves or holes and the geometrical center to be in the same longitudinal axis;

the method further comprising determining a positional relationship between the outlet of the loading device and the center of the image capturing device to obtain a spatial coordinate difference value between the outlet of the loading device and the center of the image capturing device in the x direction and/or in the y direction; and after causing the actual central position of the grooves or holes and the geometrical center to be in the same longitudinal axis, based on the obtained spatial coordinate difference value between the outlet of the loading device and the center of the image capturing device, moving the medical appliance in the x direction and/or in the y direction to cause the outlet of the loading device and the actual central position of the grooves or holes to be in the same longitudinal axis, or moving the outlet of the loading device in the x direction and/or in the y direction to cause the outlet of the loading device and the geometrical center to be in the same longitudinal axis.

16. The method according to claim 14, characterized in, in step 4), moving the image capturing device in the x direction and/or in the y direction based on the coordinate difference value between the spatial coordinate of the central position of the pattern of the grooves or holes and the spatial coordinate of the geometrical center to cause the actual central position of the grooves or holes and the geometrical center to be in the same longitudinal axis;

the method further comprising predetermining a positional relationship between the outlet of the loading device and the center of the image capturing device to obtain the spatial coordinate difference value between the outlet of the loading device and the center of the image capturing device in the x direction and/or the y direction; and after causing the actual center position of the grooves or holes and the geometrical center to be in the same longitudinal axis, based on the obtained spatial coordinate difference value between the outlet of the loading device and the center of the image capturing device, moving the medical appliance in the x direction and/or in the y direction to cause the outlet of the loading device and the actual central position of the grooves or holes to be in the same longitudinal axis, or moving the outlet of the loading device in the x direction and/or in the y direction to cause the outlet of the loading device and the geometrical canter to be in the same longitudinal axis.

17. The method according to claim 11, characterized in further comprising step 6) of moving the medical appliance back to a position where the image of the medical appliance is captured in step 2), then rotating the medical appliance by a certain angle and/or translating the medical appliance by a certain step pitch, and then performing step 2) to step 6) repeatedly till the medicament and/or polymer is dispensed to all the grooves or holes of the medical appliance.

18. The device according to claim 1, characterized in that the device further comprises a base and a gantry that is disposed on the base and extends perpendicular to the base, wherein the medical appliance platform is disposed on the base, and wherein the loading device and the image capturing device are disposed on the gantry.

* * * * *